(12) United States Patent
Harada et al.

(10) Patent No.: US 11,156,576 B2
(45) Date of Patent: Oct. 26, 2021

(54) GAS SENSOR AND METHOD OF USING THE SAME

(71) Applicant: FUJITSU LIMITED, Kawasaki (JP)

(72) Inventors: Naoki Harada, Atsugi (JP); Shintaro Sato, Atsugi (JP); Kenjiro Hayashi, Hadano (JP); Junichi Yamaguchi, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 233 days.

(21) Appl. No.: 15/854,901

(22) Filed: Dec. 27, 2017

(65) Prior Publication Data

US 2018/0136157 A1  May 17, 2018

Related U.S. Application Data

(63) Continuation of application No. PCT/JP2016/069267, filed on Jun. 29, 2016.

(30) Foreign Application Priority Data

Jun. 30, 2015  (JP) .............................. JP2015-131229

(51) Int. Cl.
*G01N 27/12* (2006.01)
*G01N 27/414* (2006.01)
*G01N 33/00* (2006.01)

(52) U.S. Cl.
CPC ....... *G01N 27/127* (2013.01); *G01N 27/4146* (2013.01); *G01N 33/0054* (2013.01); *G01N 27/4141* (2013.01); *Y02A 50/20* (2018.01)

(58) Field of Classification Search
CPC ............. G01N 27/127; G01N 27/4146; G01N 33/0054; G01N 27/4141; Y02A 50/246
See application file for complete search history.

(56) References Cited

U.S. PATENT DOCUMENTS

| | | | |
|---|---|---|---|
| 2010/0025660 A1 | 2/2010 | Jain | |
| 2010/0079130 A1 | 4/2010 | Hong | |
| 2011/0138882 A1* | 6/2011 | Moon | ................... G01N 27/12 73/31.06 |
| 2011/0210751 A1 | 9/2011 | Hong | |
| 2012/0171775 A1 | 7/2012 | Vogt | |
| 2013/0126947 A1 | 5/2013 | Wilbertz | |

(Continued)

FOREIGN PATENT DOCUMENTS

| | | | |
|---|---|---|---|
| JP | S60-181645 A | 9/1985 | |
| JP | S61-033645 A | 2/1986 | |

(Continued)

OTHER PUBLICATIONS

Office Action of Chinese Patent Application No. 201680038272.8 dated Aug. 2, 2019 sheets, (6 sheets translation, 14 sheets total).

(Continued)

*Primary Examiner* — Peter J Macchiarolo
*Assistant Examiner* — Anthony W Megna Fuentes
(74) *Attorney, Agent, or Firm* — Kratz, Quintos & Hanson, LLP

(57) ABSTRACT

A gas sensor includes: a semiconductor layer; a graphene film provided above the semiconductor layer and having at least a portion in contact with gas; and a barrier film between the semiconductor layer and the graphene film.

7 Claims, 13 Drawing Sheets

(56) References Cited

U.S. PATENT DOCUMENTS

| | | |
|---|---|---|
| 2013/0186178 A1 | 7/2013 | Usagawa |
| 2014/0151631 A1 | 6/2014 | Duesberg |
| 2014/0260545 A1* | 9/2014 | Ruhl ................... G01N 27/124 73/31.05 |

FOREIGN PATENT DOCUMENTS

| | | |
|---|---|---|
| JP | H09-159633 A | 6/1997 |
| JP | 2000-065773 A | 3/2000 |
| JP | 2009-300297 A | 12/2009 |
| JP | 2010-078604 A | 4/2010 |
| JP | 2011-169634 A | 9/2011 |
| JP | 2012073154 A | 4/2012 |
| JP | 2012-202864 A | 10/2012 |
| JP | 2012-247189 A | 12/2012 |
| JP | 2013-108987 A | 6/2013 |
| JP | 5462219 B2 | 4/2014 |
| WO | 2012150884 A1 | 11/2012 |
| WO | 2014/060894 A2 | 4/2014 |
| WO | 2015007947 A1 | 1/2015 |

OTHER PUBLICATIONS

Office Action of Japanese Patent Application No. 2017-526396 dated Nov. 6, 2018 sheets, (4 pages, 3 pages translation, 7 pages total).

D.J. Kearney, et al.; "Breath Ammonia Measurement in Helicobacter pylori Infection;" Digestive Diseases and Sciences; vol. 47; No. 11; Nov. 2002; pp. 2523-2530 (8 Sheets)/p. 2 of specification.

I. Lundström, et al.; "A hydrogen-sensitive MOS field-effect transistor;" Applied Physics Letters; vol. 26; No. 2; Jan. 15, 1975; pp. 55-57 and cover sheet (4 Sheets)/p. 3 of specification.

I. Ludström, et al.; "Catalytic Metals and Field-effect Devices—a Useful Combination;" Sensors and Actuators, B1; vol. 1; 1990; pp. 15-20 (6 Sheets)/p. 3 of specification.

F. Schedin, et al.; "Detection of individual gas molecules adsorbed on graphene;" Nature Materials; vol. 6; Sep. 2007; pp. 652-655 and pp. 1-6 of Supplemental Information (10 Sheets total)/p. 3 of specification.

H.J. Yoon, et al.; "Carbon dioxide gas sensor using a graphene sheet;" Sensors and Actuators B; vol. 157; 2011; pp. 310-313 (4 Sheets)/p. 3 of specification.

M. Gautam, et al.; "Gas sensing properties of graphene synthesized by chemical vapor deposition;" Materials Science and Engineering C; vol. 31; 2011; pp. 1405-1411 (7 Sheets total)/p. 3 of specification.

S. Sato, et al.; Growth of diameter-controlled carbon nanotubes using monodisperse nickel nanoparticles obtained with a differential mobility analyzer, Chemical Physics Letters; vol. 382; 2003; pp. 361-366 (6 Sheets total).

S. Sato, et al.; "Fabrication of Carbon Nanotube via Interconnects at Low Temperature and Their Robustness over a High-Density Current" Sensors and Materials; vol. 21; No. 7; 2009; pp. 373-383 (11 Sheets).

International Search Report for International Application No. PCT/JP2016/069267 dated Sep. 20, 2016.

Written Opinion of the International Searching Authority for International Application No. PCT/JP2016/069267 dated Sep. 20, 2016 (5 Sheets, 3 Sheets translation, 8 Sheets total).

Office Action of Japanese Patent Application No. 2017-526396 dated Jul. 2, 2019 (6 pages, 6 pages translation, 12 pages total).

* cited by examiner

GAS SENSOR AND METHOD OF USING THE SAME

CROSS-REFERENCE TO RELATED APPLICATION

This application is a continuation application of International Application PCT/JP2016/069267 filed on Jun. 29, 2016 and designated the U.S., which claims the benefit of priority of the prior Japanese Patent Application No. 2015-131229, filed on Jun. 30, 2015, the entire contents of which are incorporated herein by reference.

FIELD

The present invention relates to a gas sensor and a method of using the same.

BACKGROUND

The gas sensor is one kind of a chemical substance sensor and detects a chemical substance contained in gas. The gas sensor is used, for example, for a medical instrument and a diagnostic device. It is known that when a human is affected with a specific disease, the content of a specific chemical substance contained in expiration varies. If the variation amount can be detected, easy and rapid diagnosis becomes possible. The easy and rapid diagnosis can contribute to health maintenance and suppression in health-care costs in an aging society.

For example, it is known that when a human is affected with gastric cancer, the ammonia concentration in expiration increases. Follow-up of the ammonia concentration is effective for determination of development of gastric cancer, and its diagnostic threshold is considered to be about 200 ppb. Accordingly, a gas sensor that can detect ammonia at the ppb level is effective for diagnosis of gastric cancer.

However, the gas sensor that can detect ammonia with a high sensitivity at the ppb level has not been developed yet. Improvement in detection sensitivity to other gas is also desired.

Patent Literature 1: Japanese Patent No. 3555739
Patent Literature 2: Japanese Laid-open Patent Publication No. 9-159633
Patent Literature 3: Japanese Patent No. 4866880
Patent Literature 4: Japanese Laid-open Patent Publication No. 2011-169634
Patent Literature 5: Japanese Laid-open Patent Publication No. 2013-108987
Patent Literature 6: Japanese Laid-open Patent Publication No. 2010-78604
Patent Literature 7: Japanese Laid-open Patent Publication No. 2012-247189
Non-Patent Literature 1: D. J. Kearney et al., Dig. Dis. Sci. 47, 2523 (2002)
Non-Patent Literature 2: I. Lundstrom et al., Appl. Phys. Lett., vol. 26, no. 2, pp. 55 (1975)
Non-Patent Literature 3: I. Lundstrom et al., Sensors and Actuators B, vol. 1, pp. 15 (1990)
Non-Patent Literature 4: F. Schedin et al., Nature Mater. Vol. 6, pp. 652 (2007)
Non-Patent Literature 5: H. J. Yoon et al., Sensors and Actuators B, vol. 157, pp. 310 (2011)
Non-Patent Literature 6: M. Gautan et al., Materials Science and Engineering C, vol. 31, pp. 1405 (2011)

SUMMARY

An aspect of the gas sensor includes: a semiconductor layer; a graphene film provided above the semiconductor layer and having at least a portion in contact with gas; and a barrier film between the semiconductor layer and the graphene film. The graphene film means a film composed or one or two or more unit layers of graphene.

An aspect of a method of using the gas sensor detects a physical amount corresponding to a variation amount in work function of the graphene film of the above-described gas sensor.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENT

Hereinafter, embodiments will be concretely described referring to the accompanying drawings.

First Embodiment

Figure 1:
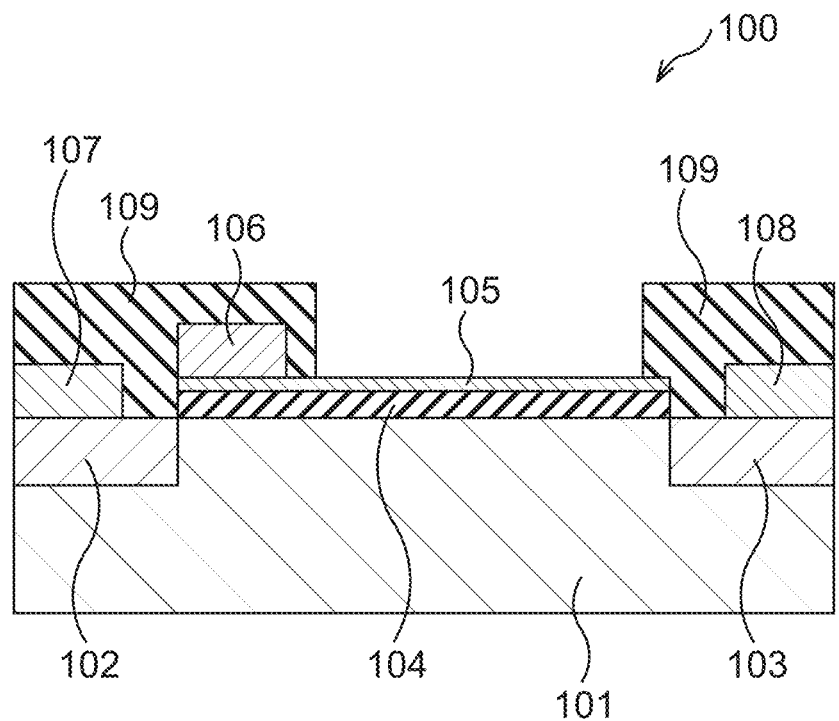
FIG. 1 is a cross-sectional view illustrating a structure of a gas sensor according to a first embodiment.

A first embodiment will be described first. FIG. 1 is a cross-sectional view illustrating a structure of a gas sensor according to the first embodiment.

A gas sensor 100 according to the first embodiment includes, as illustrated in FIG. 1, a p-type layer 101, an insulating film 104 on the p-type layer 101, and a graphene film 105 on the insulating film 104. The gas sensor 100 includes an n-type layer 102 and an n-type layer 103 which are in the surface of the p-type layer 101. The n-type layer 102 and the n-type layer 103 hold the insulating film 104 and the graphene film 105 therebetween in a plan view. The gas sensor 100 includes a gate electrode 106 on the graphene film 105, a source electrode 107 on the n-type layer 102, and a drain electrode 108 on the n-type layer 103. The gas sensor 100 includes a protective film 109 covering the gate electrode 106, the source electrode 107, and the drain electrode 108. A portion of the graphene film 105 is exposed from the protective film 109 and is exposed to gas. The p-type layer 101 is an example of a semiconductor layer, and the insulating film 104 is an example of a barrier film.

Figure 2:
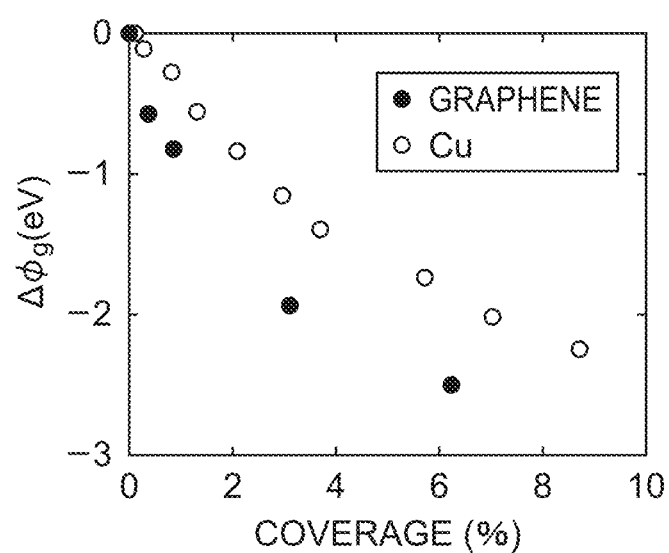
FIG. 2 is a chart illustrating the relation between a coverage by ammonia molecules and a variation amount in work function of graphene.

Here, the property of graphene will be described. When ammonia molecules ($NH_3$) are adsorbed to graphene, the ammonia molecules act as donors with respect to graphene so that graphene is n-doped. A work function of the graphene adsorbing the ammonia molecules can be found by a first-principles calculation method using a density functional theory. FIG. 2 is a chart illustrating the relation between a coverage by the ammonia molecules and a variation amount $\Delta\phi_g$ in work function of graphene before and after adsorption of the ammonia molecules. The coverage is a percentage (%) of the number of adsorbed molecules to the number of surface atoms. As illustrated in FIG. 2, with an increase in coverage, namely, with an increase in the number of adsorbed molecules, the work function of graphene decreases. In FIG. 2, a variation amount in work function in the case where potassium (K) being an alkali metal atom corresponding to a positive monovalent charge is adsorbed to the surface of a copper (Cu) layer, for comparison. This variation amount is obtained by referring to a literature cited (MURATA Yoshimasa, YAGI Katsumichi, HATTORI Takeo, "Physical Properties of Solid Surface and Interface", BAIFUKAN (1999), pp 81-83).

As illustrated in FIG. 2, the variation amount in work function of graphene is large as compared with that of metal, and is twice or more in particular when the coverage is low. This can be construed as follows. The variation in work function is considered to be caused from (1) the effect of a dipole by movement of electric charges from the adsorbed molecules, and (2) the effect of an increase in Fermi level by the n-doping. When the doped electron concentration is $\rho$, an increase amount $\Delta E_F$ of the Fermi level by (2) is about $\rho/D$. Here, D is the density of states of a substance. Since the density of states of graphene becomes 0 at the Fermi level, the increase amount $\Delta E_F$ becomes comparatively large. On the other hand, the density of states in metal such as copper is generally large at the Fermi level, so that the increase amount $\Delta E_F$ is small. For this reason, the variation amount in work function of graphene is considered to become large as compares with that of metal.

Accordingly, when the ammonia molecules are adsorbed to the graphene film 105 in the first embodiment, the work function of the graphene film 105 largely varies even if the amount of ammonia molecules is small. Therefore, detection of the amount of the variation makes it possible to detect the amount of ammonia molecules adsorbed to the graphene film 105 with high accuracy, thereby specifying the concentration of ammonia in an environment with high accuracy.

Figure 3A:
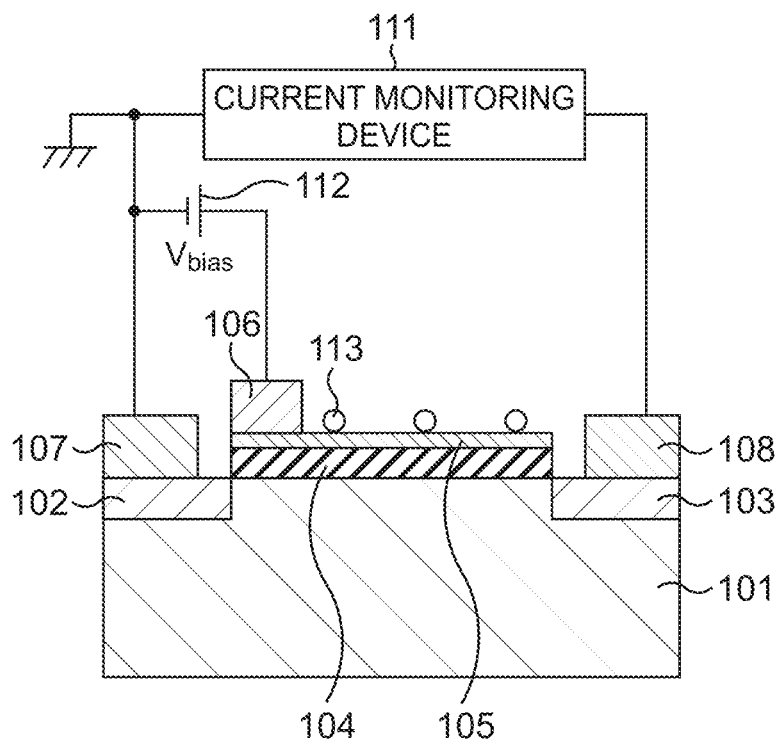
FIG. 3A is a view illustrating a method of using the gas sensor according to the first embodiment.

Next, a method of using the gas sensor 100 will be described. FIG. 3A is a view illustrating the method of using the gas sensor according to the first embodiment.

As illustrated in FIG. 3A, the gas sensor 100 is used with a current monitoring device 111 connected, for example, between the source electrode 107 and the drain electrode 108, the current monitoring device 111 detecting the current flowing between the source electrode 107 and the drain electrode 108. The source electrode 107 is grounded, and a bias voltage $V_{bias}$ is applied to the gate electrode 106 from a bias power supply 112. The current monitoring device 111 may include, for example, various kinds of power supplies, an amplifier circuit, a sampling circuit, an analog-digital (AD) converter, a data processing computer and the like.

Figure 3B:
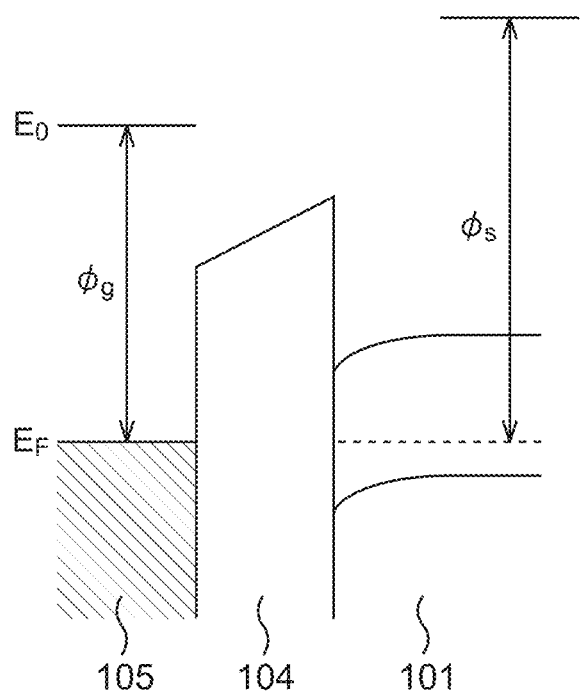
FIG. 3B is a chart illustrating a band structure of a graphene film, an insulating film, and a p-type layer.

FIG. 3B illustrates a band chart of the graphene film 105, the insulating film 104, and the p-type layer 101. Between a work function $\phi_g$ of the graphene film 105 and a Fermi level $\phi_s$ of the p-type layer 101, the following relation is established using a flat band voltage $V_{FB}$.

$$V_{FB} = \phi_g - \phi_s$$

When the graphene film 105 adsorbs ammonia molecules 113 being molecules to be detected, the ammonia molecules 113 act as donors with respect to the graphene film 105, so that the graphene film 105 is n-doped. As a result, the work function of the graphene film 105 varies and the flat band voltage also varies. When a variation amount in work function of the graphene film 105 is $\Delta\phi_g$ and a variation amount in flat band voltage is $\Delta V_{FB}$, the following relation is established.

$$\Delta V_{FB} = \Delta\phi_g$$

Figure 4:
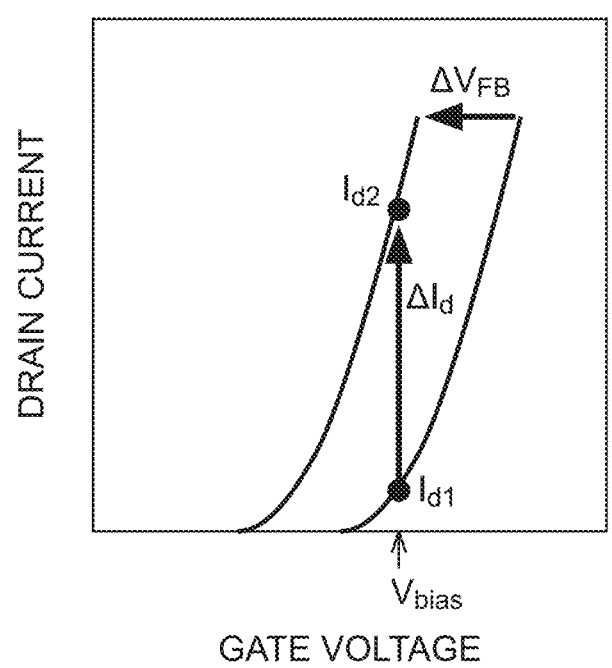
FIG. 4 is a chart illustrating the relation between a variation in flat band voltage and a variation in drain current.

When the flat band voltage varies, a drain current at the same bias point $V_{bias}$ varies only by $\Delta I_d$ from $I_{d1}$ to $I_{d2}$ as illustrated in FIG. 4. Detection of this variation amount $\Delta I_d$ by the current monitoring device 111 makes it possible to specify the number of ammonia molecules 113 adsorbed to the graphene film 105, and specify the concentration of ammonia from the number. The variation amount $\Delta I_d$ is an example of the physical amount.

The variation amount $\Delta I_d$ depends on a mutual conductance, so that, for example, when a voltage in a sub-threshold region is used as the bias voltage $V_{bias}$, the drain current varies exponentially. Accordingly, even if the variation amount in work function of the graphene film 105 is small, the variation amount $\Delta I_d$ in the drain current can be made large. For example, in the case where the variation amount in work function is 60 mV, a single-digit variation amount, namely, 1000% can be obtained as $\Delta I_d/I_{d1}$. Besides, for example, when a voltage in an ON region is used as the bias voltage $V_{bias}$, an absolute variation in drain current can be set to near the maximum current of a field effect transistor. According to the above embodiment, ammonia at a ppb level can be easily detected.

Note that when the graphene film 105 adsorbs the ammonia molecules 113, the electrical conductivity of the graphene film 105 varies depending on the amount of the ammonia molecules 113. Therefore, it is not impossible to specify the concentration of ammonia by detecting the variation in electrical conductivity. However, since the variation in electrical conductivity is very small as compared with the variation in work function, the concentration of ammonia cannot be detected with high sensitivity.

The number of unit layers of graphene contained in the graphene film 105 is not limited, but is preferably 1 to 100 and particularly preferably 1 in consideration of the ease of production process and the (parasitic) resistance of the graphene film 105 itself. Further, to obtain higher sensitivity, a larger area of a portion of the graphene film 105 in contact with gas, as compared with an area of a portion covered by the protective film or the electrode, is more preferable.

Next, a method of manufacturing the gas sensor according to the first embodiment will be described. FIG. 5A to FIG. 5F are cross-sectional views illustrating the method of manufacturing the gas sensor according to the first embodiment in order of steps.

Figure 5A:
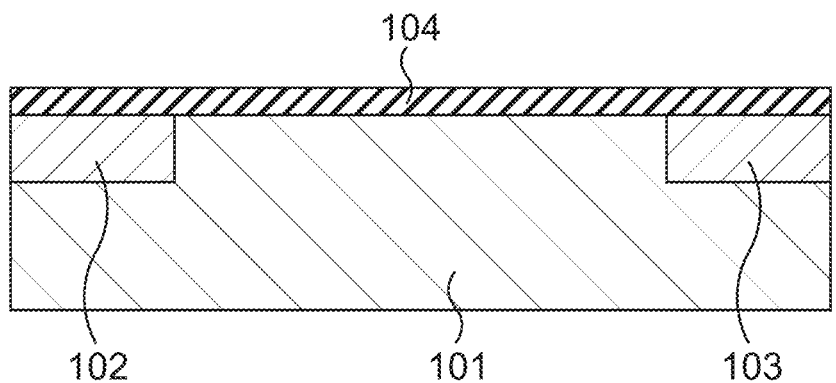
FIG. 5A is a cross-sectional view illustrating a method of manufacturing the gas sensor according to the first embodiment.

First, as illustrated in FIG. 5A, the n-type layer 102 and the n-type layer 103 are formed in the surface of the p-type layer 101. For example, the p-type layer 101 can be formed by ion implantation of p-type impurities into a surface of a silicon substrate, and the n-type layer 102 and the n-type layer 103 can be formed by ion implantation of n-type impurities to a surface of the p-type layer 101. Subsequently, the insulating film 104 is formed on the p-type layer 101, the n-type layer 102, and the n-type layer 103. The insulating film 104 can be formed, for example, by thermal oxidation of the surfaces of the p-type layer 101, the n-type layer 102, and the n-type layer 103.

Figure 5B:
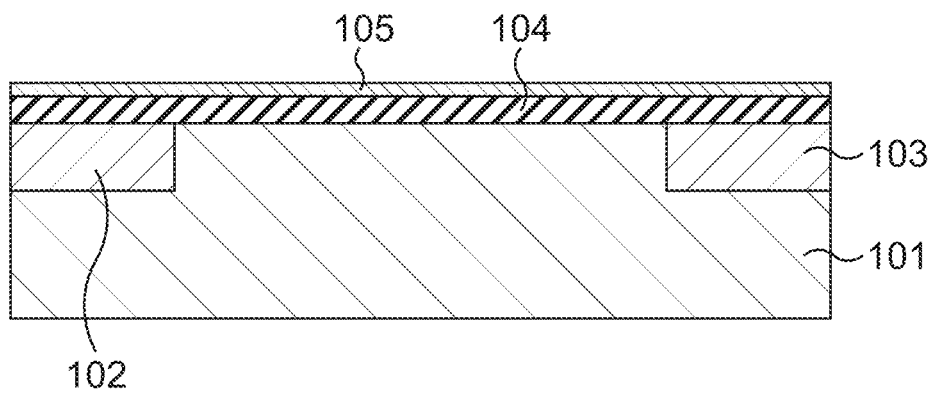
FIG. 5B is a cross-sectional view illustrating the method of manufacturing the gas sensor, subsequent to FIG. 5A.

Thereafter, as illustrated in FIG. 5B, the graphene film 105 is provided on the insulating film 104. The graphene film 105 can be formed, for example, by growth and transfer on a later-described growth substrate.

Figure 5C:
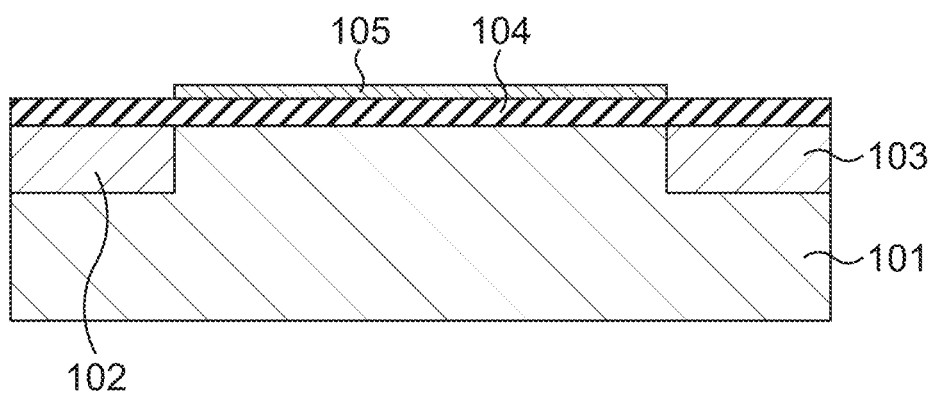
FIG. 5C is a cross-sectional view illustrating the method of manufacturing the gas sensor, subsequent to FIG. 5B.

Subsequently, as illustrated in FIG. 5C, the graphene film 105 is patterned. The graphene film 105 can be patterned, for example, by a photolithography technique and an etching technique. An example of the etching technique is a reactive ion etching (RIE) using oxygen plasma.

Figure 5D:
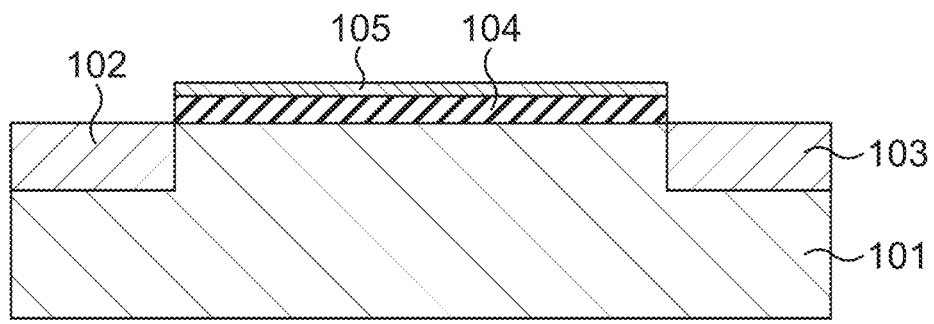
FIG. 5D is a cross-sectional view illustrating the method of manufacturing the gas sensor, subsequent to FIG. 5C.

Subsequently, as illustrated in FIG. 5D, the insulating film 104 is patterned to expose at least a portion of the n-type layer 102 and at least a portion of the n-type layer 103. The insulating film 104 can be patterned, for example, by a photolithography technique and an etching technique.

Figure 5E:
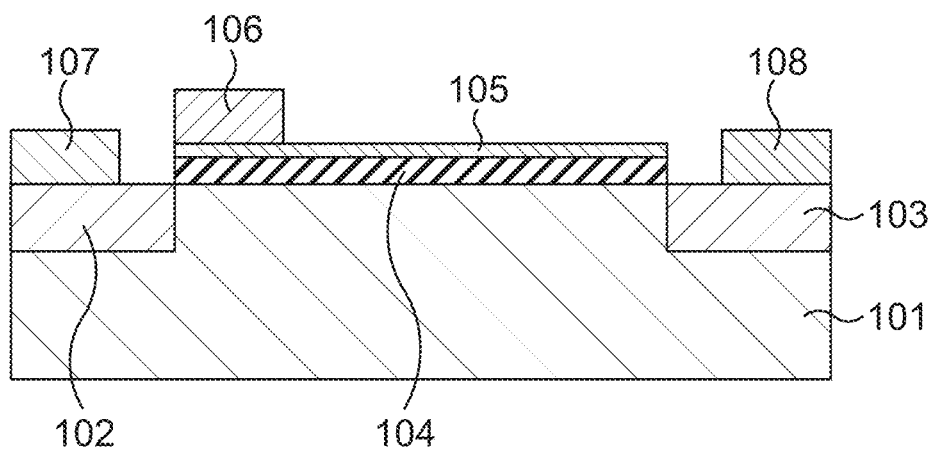
FIG. 5E is a cross-sectional view illustrating the method of manufacturing the gas sensor, subsequent to FIG. 5D.

Thereafter, as illustrated in FIG. 5E, the gate electrode 106 is formed on the graphene film 105, the source electrode 107 is formed on the n-type layer 102, and the drain electrode 108 is formed on the n-type layer 103. In the formation of the gate electrode 106, the source electrode 107, and the drain electrode 108, for example, a mask exposing regions planned for forming them is formed, a metal film is formed by a vacuum deposition method, and the mask is removed together with the metal film thereon. In other words, the gate electrode 106, the source electrode 107, and the drain electrode 108 can be formed by a lift-off method. In formation of the metal film, for example, a Ti film with a thickness of 5 nm is formed and an Au film with a thickness of 200 nm is formed thereon.

Figure 5F:
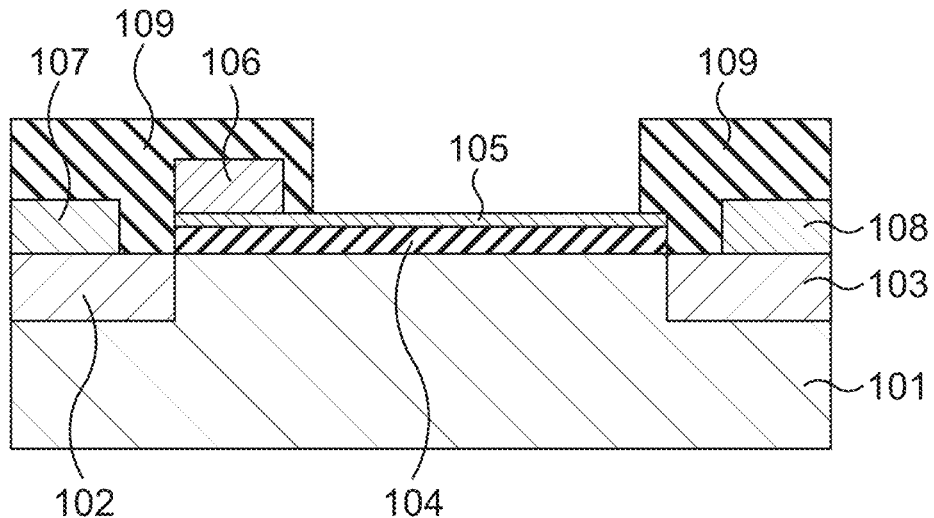
FIG. 5F is a cross-sectional view illustrating the method of manufacturing the gas sensor, subsequent to FIG. 5E.

Subsequently, as illustrated in FIG. 5F, the protective film 109 covering the gate electrode 106, the source electrode 107, and the drain electrode 108 and exposing at least a portion of the graphene film 105 is formed.

Thus, the gas sensor according to the first embodiment can be manufactured.

Here, a method of providing the graphene film 105 on the insulating film 104 will be described. FIG. 6A to FIG. 6D are cross-sectional views illustrating the method of providing the graphene film 105 on the insulating film 104 in order of steps.

Figure 6A:
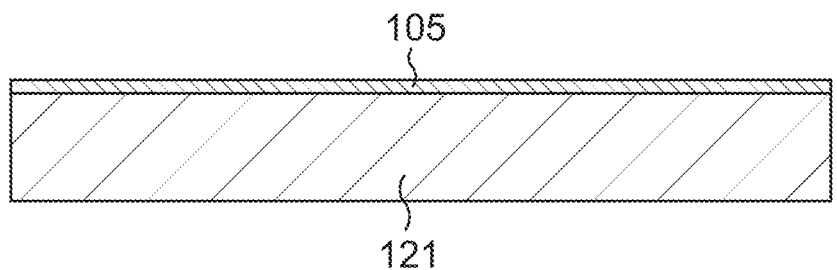
FIG. 6A is a cross-sectional view illustrating a method of providing the graphene film on the insulating film.

First, as illustrated in FIG. 6A, the graphene film 105 is grown on a growth substrate 121 having a catalytic action. As the growth substrate 121, for example, a Cu substrate can be used. The graphene film 105 can be grown using, for example, a chemical vapor deposition (CVD) synthesis furnace. In this event, for example, the temperature of the growth substrate 121 is set to 1000° C., a mixed gas of $H_2$ and $CH_4$ is used as a source gas, the flow rate of $H_2$ is set to be 500 times the flow rate of $CH_4$, and the total pressure is set to 760 Torr.

Figure 6B:
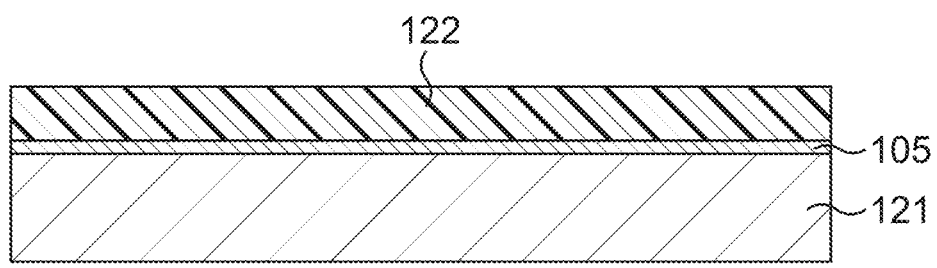
FIG. 6B is a cross-sectional view illustrating the method of providing the graphene film on the insulating film, subsequent to FIG. 6A.

Subsequently, as illustrated in FIG. 6B, a support 122 is formed on the graphene film 105. As the support 122, for example, a polymethyl methacrylate (PMMA) film can be used.

Figure 6C:
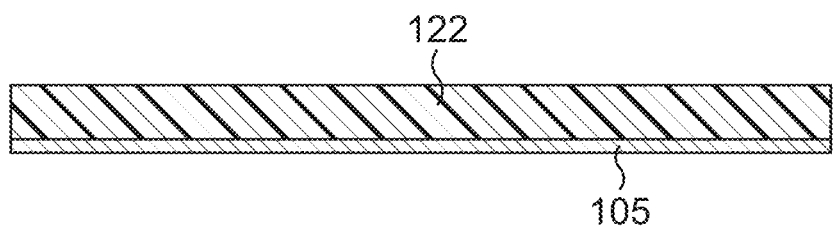
FIG. 6C is a cross-sectional view illustrating the method of providing the graphene film on the insulating film, subsequent to FIG. 6B.

Subsequently, as illustrated in FIG. 6C, the growth substrate 121 is removed. The growth substrate 121 can be dissolved, for example, with an iron chloride solution.

Figure 6D:
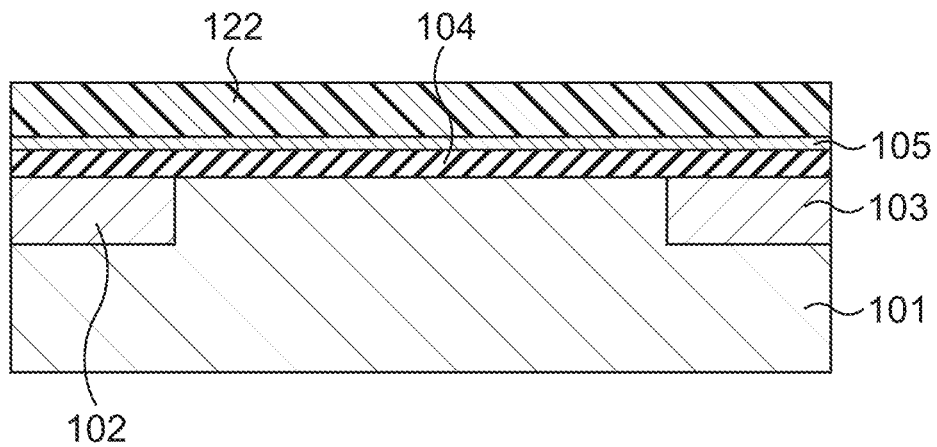
FIG. 6D is a cross-sectional view illustrating the method of providing the graphene film on the insulating film, subsequent to FIG. 6C.

Subsequently, as illustrated in FIG. 6D, the graphene film 105 is placed on the insulating film 104. Then, the support 122 is removed using an organic solvent.

Thus, the graphene film 105 can be provided on the insulating film 104 by transfer.

Figure 7:
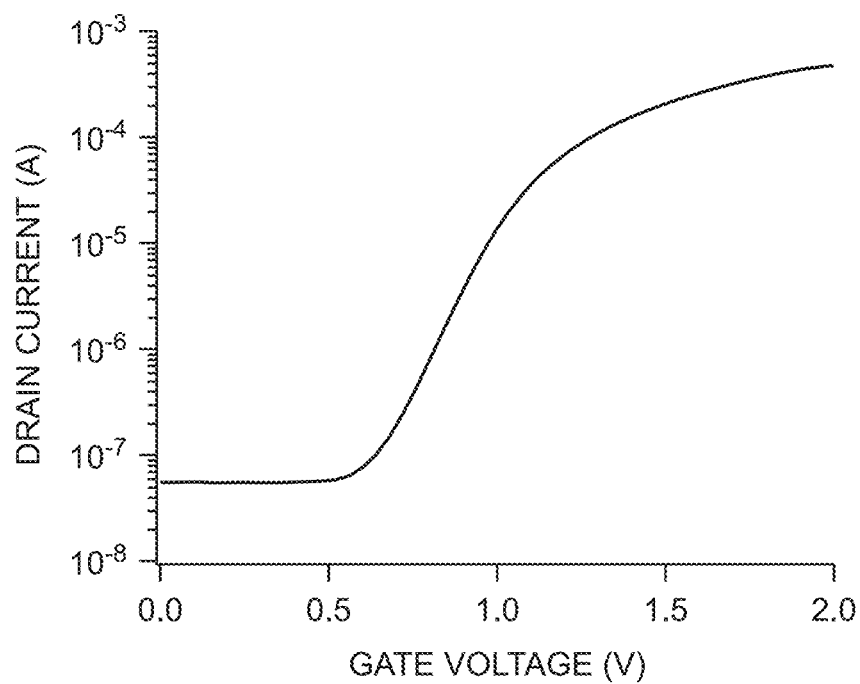
FIG. 7 is a chart illustrating dependence of the drain current on a gate voltage in the gas sensor according to the first embodiment.

Here, the experiment carried out for the first embodiment by the present inventors will be explained. The present inventors manufactured the gas sensor according to the first embodiment and measured the dependence of the drain current on the gate voltage. FIG. 7 illustrates its result. A channel length of the gas sensor was set to about 5 μm, a thickness of a gate oxide film was set to about 14 nm, and the drain voltage was set to 1 V. A transistor included in the gas sensor is an enhanced type.

Figure 8:
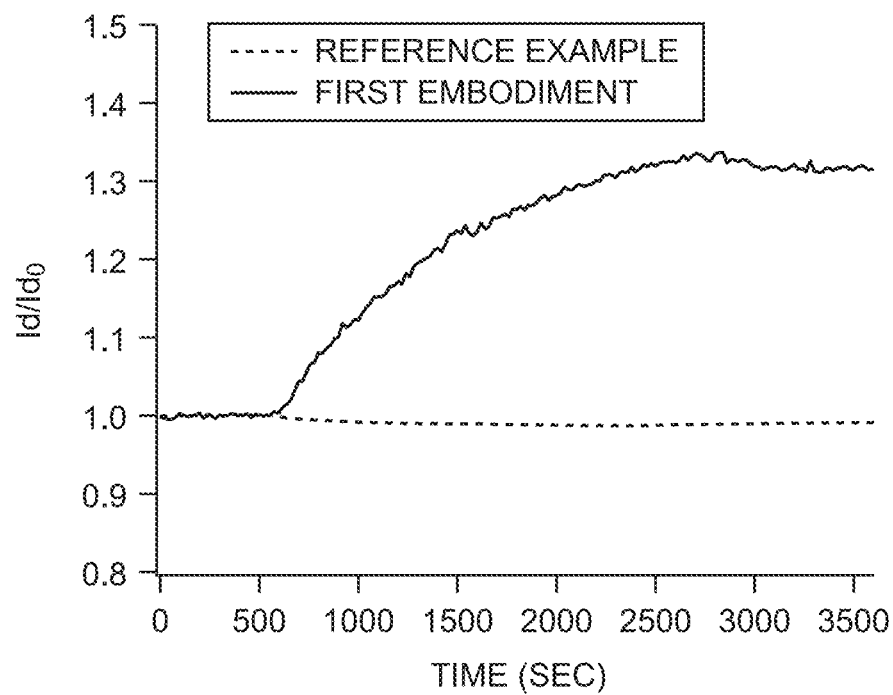
FIG. 8 is a chart illustrating sensitivity to ammonia in the first embodiment and in a reference example.

Next, the gas sensor was placed in a measurement chamber and 1 ppm of ammonia was introduced, and the variation in drain current was observed. For comparison, similar observation using a gas sensor (reference example) using graphene for its channel was also carried out. FIG. 8 illustrates their results. The horizontal axis in FIG. 8 represents elapsed time and the vertical axis represents the percentage ($Id/Id_0$) of the drain current Id to the drain current $Id_0$ at start of measurement. In this observation, the gate voltage was set to 800 mV and the drain voltage was set to 1 V. As illustrated in FIG. 8, the percentage of variation in drain current is about 1% in the reference example, whereas a percentage of variation of several tens of percent was obtained in the gas sensor according to the first embodiment. This means that the gas sensor according to the first embodiment exhibits much higher sensitivity with respect to ammonia than that in the reference example.

Figure 9:
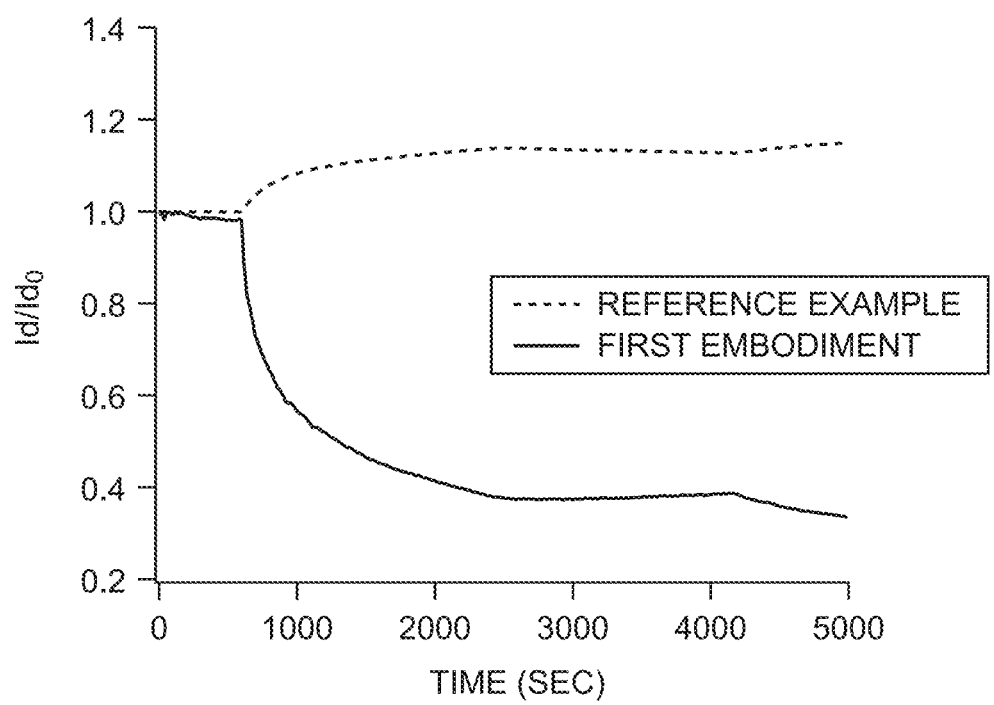
FIG. 9 is a chart illustrating sensitivity to nitrogen dioxide in the first embodiment and in the reference example.

Further, the gas sensor was placed in the measurement chamber and 1 ppm of nitrogen dioxide was introduced, and the variation in drain current was observed similarly to the above. For comparison, similar observation using the gas sensor (reference example) using graphene for its channel was also carried out. FIG. 9 illustrates their results. As illustrated in FIG. 9, a percentage of variation in drain current much larger than that in the reference example was exhibited in the gas sensor according to the first embodiment. This means that the gas sensor according to the first embodiment exhibits much higher sensitivity also with respect to nitrogen dioxide than that in the reference example.

Second Embodiment

Figure 10:
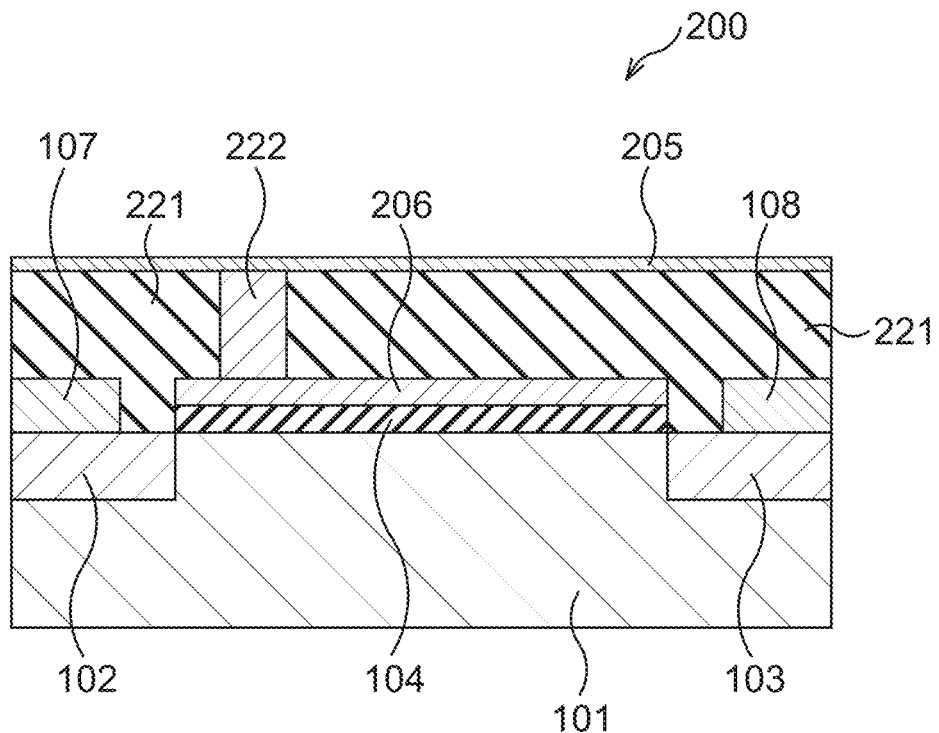
FIG. 10 is a cross-sectional view illustrating a structure of a gas sensor according to a second embodiment.

Next, a second embodiment will be described. FIG. 10 is a cross-sectional view illustrating a structure of a gas sensor according to the second embodiment.

A gas sensor 200 according to the second embodiment includes, as illustrated in FIG. 10, a p-type layer 101, an n-type layer 102, an n-type layer 103, an insulating film 104, a source electrode 107, and a drain electrode 108 as in the first embodiment. The gas sensor 200 further includes a gate electrode 206 on the insulating film 104, an interlayer insulating film 221 covering the insulating film 104 and the like, and a conductive layer 222 provided in the interlayer insulating film 221 and being in contact with the gate electrode 206. The gas sensor 200 includes a graphene film 205 covering the upper surfaces of the interlayer insulating film 221 and the conductive layer 222 and being in contact with the conductive layer 222. The graphene film 205 is in electrical contact with the insulating film 104 through the conductive layer 222 in the interlayer insulating film 221. Examples of the material of the gate electrode 206 include polycrystalline Si and metal. The conductive layer 222 is a conductive via such as a metal via.

When ammonia molecules are adsorbed to the graphene film 205 in the second embodiment, the work function of the graphene film 205 largely varies even if the amount of ammonia molecules is small. Since the graphene film 205 is in contact with the conductive layer 222 and the conductive layer 222 is in contact with the gate electrode 206, the work function of the graphene film 205 is transmitted to the gate electrode 206. Accordingly, a variation amount $\Delta I_d$ in drain current corresponding to the variation amount in work function of the graphene film 205 can be measured as in the first embodiment. Further, an area of a portion of the graphene film 205 in contact with gas in the second embodiment is larger than an area of a portion of the graphene film 105 in contact with gas in the first embodiment. Therefore, according to the second embodiment, the concentration of ammonia can be measured with higher sensitivity.

Third Embodiment

Figure 11:
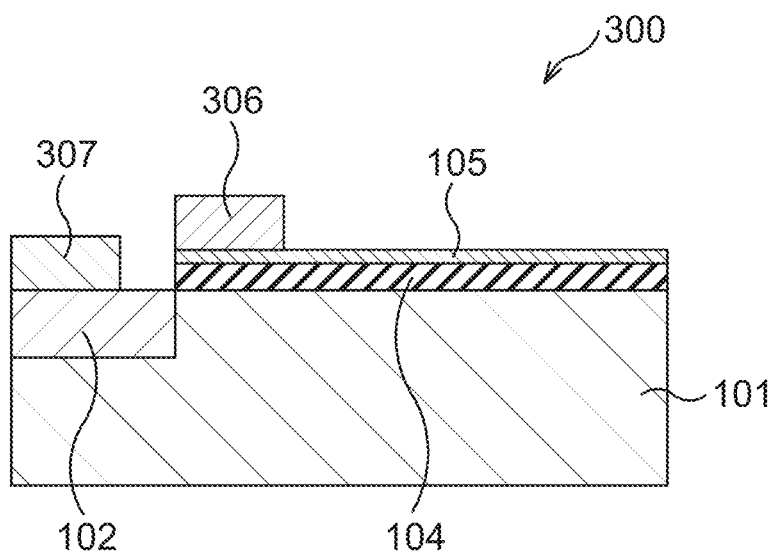
FIG. 11 is a cross-sectional view illustrating a structure of a gas sensor according to a third embodiment.

Next, a third embodiment will be described. FIG. 11 is a cross-sectional view illustrating a structure of a gas sensor according to the third embodiment.

A gas sensor 300 according to the third embodiment includes, as illustrated in FIG. 11, a p-type layer 101, an n-type layer 102, an insulating film 104, and a graphene film 105 as in the first embodiment. The gas sensor 300 further includes an electrode 306 similar to the gate electrode 106 and an electrode 307 similar to the source electrode 107.

In the third embodiment, the variation amount in work function of the graphene film 105 accompanying the adsorption of the ammonia molecules, namely, the variation amount in flat band voltage is exhibited as a variation amount $\Delta C$ in electric capacity between the electrode 306 and the electrode 307. Therefore, measurement of the variation amount $\Delta C$ makes it possible to specify the concentration of ammonia. According to the third embodiment, size reduction and cost reduction accompanying the size reduction with respect to the first embodiment are possible. Further, since the measurement is possible without passing drain current, power saving is also possible. The variation amount $\Delta C$ is an example of the physical amount.

Fourth Embodiment

Figure 12A:
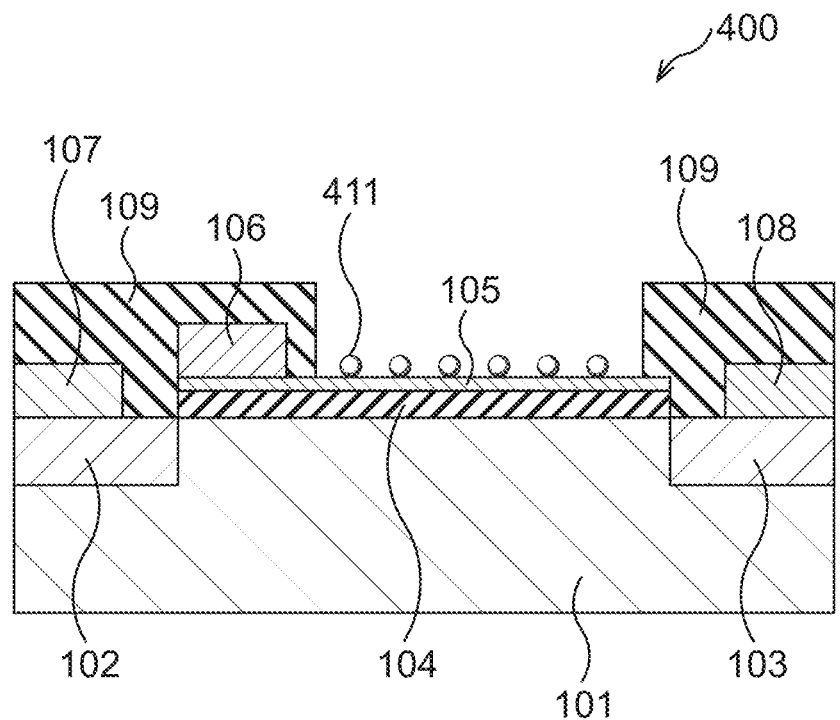
FIG. 12A is a cross-sectional view illustrating a structure of a gas sensor according to a fourth embodiment.

Next, a fourth embodiment will be described. FIG. 12A is a cross-sectional view illustrating a structure of a gas sensor according to the fourth embodiment.

A gas sensor 400 according to the fourth embodiment includes, as illustrated in FIG. 12A, nanoparticles 411 varying the work function of graphene on a graphene film 105. The other configuration is the same as that in the first embodiment. For example, the particle diameter of the nanoparticle 411 is, but not limited to, about 1 nm to 100 nm, and the coverage of the graphene film 105 by the nanoparticles 411 is, but not limited to, about 5% to 100%. Examples of the material of the nanoparticles 411 include metals such as gold, silver, copper, scandium, titanium, vanadium, chromium, manganese, iron, cobalt, nickel, zinc, aluminum, yttrium, zirconium, niobium, molybdenum, ruthenium, rhodium, palladium, hafnium, tantalum, tungsten, osmium, iridium, platinum and the like. As the material of the nanoparticles 411, oxides of those metals may be used. As the material of the nanoparticles 411, semiconductors such as silicon, germanium, zinc oxide, and tin oxide may be used. A plurality of kinds of nanoparticles 411 made of different materials may exist in a mixed manner on the graphene film 105.

In the fourth embodiment, since the work function of graphene varies due to the nanoparticles 411, the sensitivity is different from that in the first embodiment so that high sensitivity can be exhibited also with respect to gas other than ammonia and nitrogen dioxide. Further, depending on the material of the nanoparticles 411, the nanoparticles 411 themselves react with the gas and the states of the nanoparticles 411 vary to thereby vary the sensitivity in some cases.

For example, palladium nanoparticle absorb hydrogen and the work function of palladium at the interface with graphene varies, resulting in variation also in work function of graphene. Therefore, the threshold voltage of the transistor varies to vary the drain current of the channel. Further, nanoparticles of nickel, cobalt or iron adsorb hydrocarbon-based gas such as methane and acetylene, so that when the nanoparticles 411 contain nickel, cobalt or iron, the gas sensor 400 can function as a gas sensor for hydrocarbon-based gas.

Figure 12B:
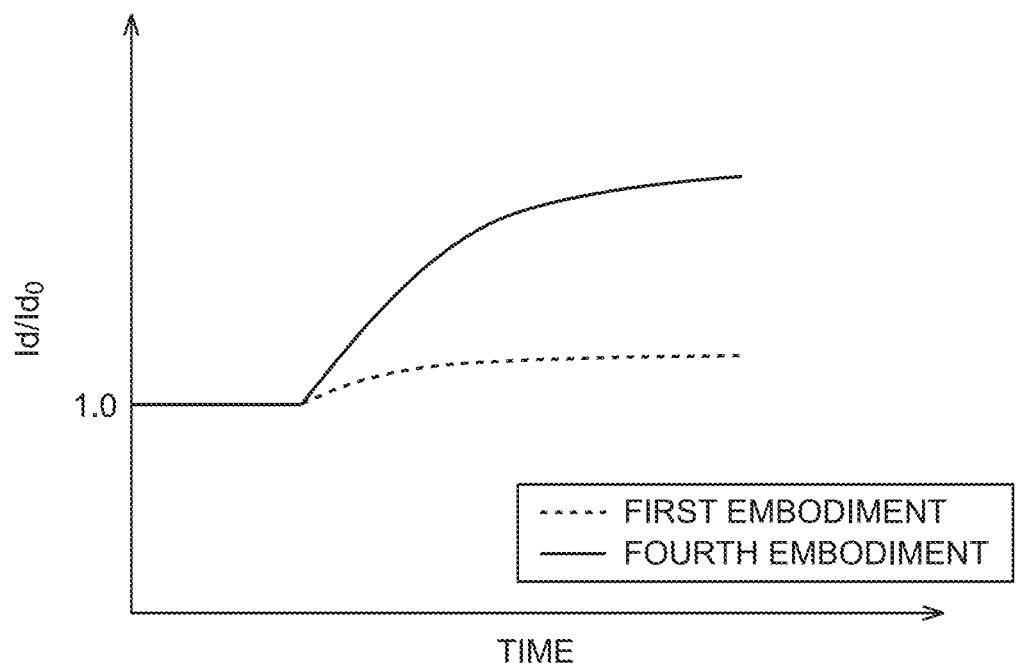
FIG. 12B is a chart illustrating sensitivity to hydrogen in the first embodiment and in the fourth embodiment.

FIG. 12B illustrates a response example of the gas sensor 400 using nanoparticles 411 of Pd. The transistor included in the gas sensor 400 is an n-channel transistor which varies in threshold voltage to the negative side due to adsorption of hydrogen thereto, so that the drain current increases if the gate voltage is the same. Therefore, the gas sensor 400 using the nanoparticles 411 of Pd exhibits sensitivity to hydrogen higher than that in the first embodiment as illustrated in FIG. 12B.

Figure 13:
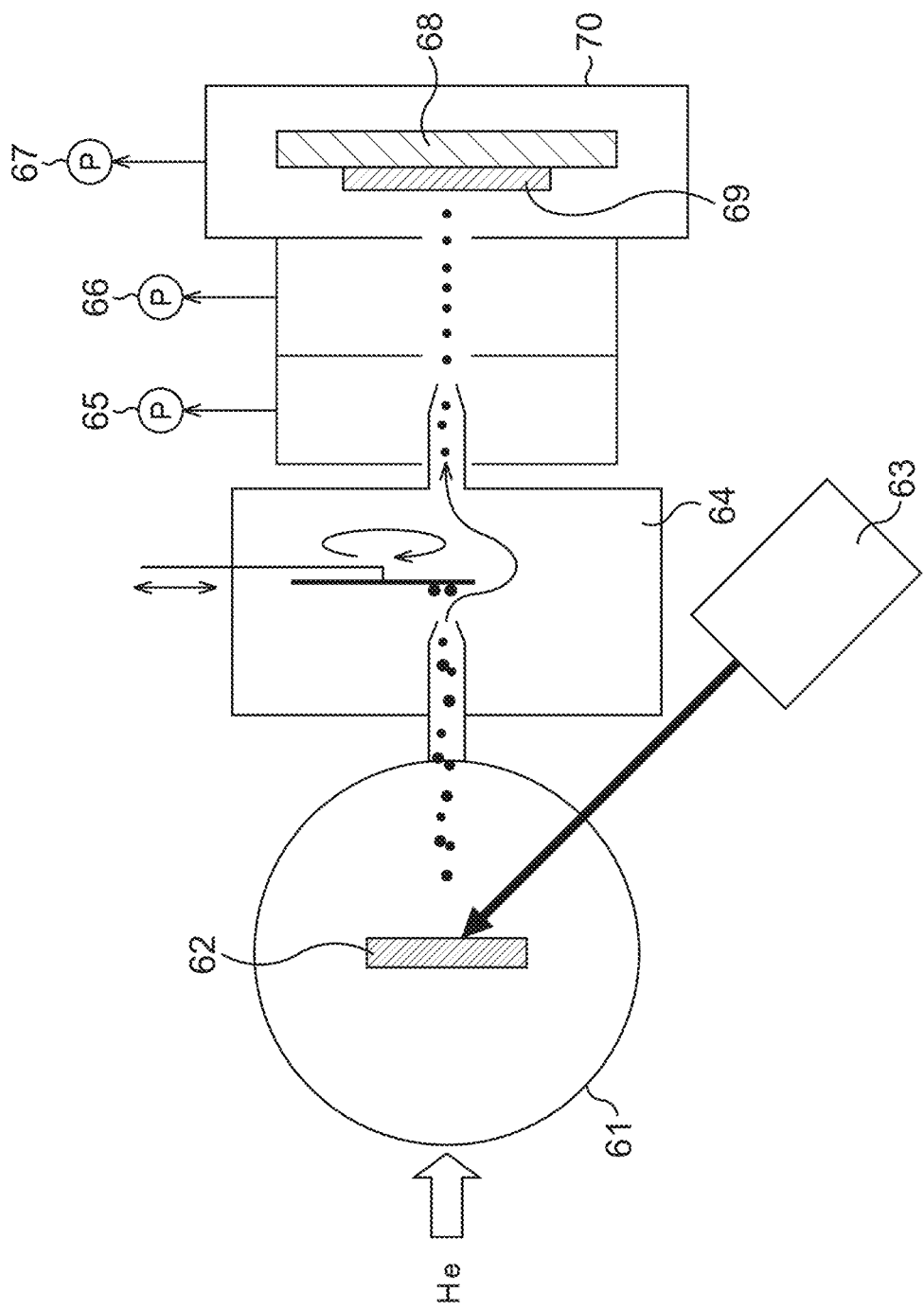
FIG. 13 is a view illustrating an example of an apparatus to be used for deposition of nanoparticles.

Here, an example of a method of depositing the nanoparticles 411 will be described. FIG. 13 is a view illustrating an example of an apparatus used for deposition of the nanoparticles 411. In the method using the apparatus, nanoparticles are generated by laser ablation in a He gas at low pressure. More specifically, a He gas at 1 slpm (standard litter per minute) to 2 slpm is introduced into a generation chamber 61 to adjust the pressure in the generation chamber 61 to about 1 kPa. Then, a metal target 62, for example, a Co target placed in the generation chamber 61 is irradiated by a pulse laser 63. Here, as the pulse laser 63, for example, a laser of a second harmonic (532 nm) of a YAG (Yttrium Aluminum Garnet) laser is used, and its power is set to 2 W and a repetition frequency of pulse is set to 20 Hz. By irradiation by the laser, metal vapor is generated from the metal target 62. When the metal vapor is rapidly cooled with the He gas, particles having a particle diameter of about 1 nm to 100 nm are formed. The particle having a particle diameter of about 1 nm to 100 nm is called a nanoparticle. The particles are sent by the He gas to a fine particle size sorting unit (impactor) 64.

The impactor 64 is an apparatus that removes particles having a certain size or more by inertia of the particles. The nanoparticles generally grow with time by aggregation, and therefore there is a lower limit in size of the nanoparticles. Accordingly, by removing nanoparticles having the certain size or more using the impactor 64, the sizes of the nanoparticles passing through the impactor 64 are controlled. Here, the impactor 64 is used, for example, under the condition that the diameters of the nanoparticles passing through the impactor 64 are about 5 nm. The nanoparticles sorted in size by the impactor 64 are thereafter guided by differential pumping using pumps 65 and 66 into a deposition chamber 70 at a pressure of about $10^{-3}$ Pa connected to a pump 67. During the process of being guided to the deposition chamber 70, the nanoparticles become a beam form and almost vertically collide with a substrate 69 placed on a stage 68, and are deposited thereon. In this method, the nanoparticles 411 are not arrayed in closest packing but take a random arrangement. This method enables deposition of the nanoparticles 411 which are strictly uniform in size and highly crystalline and having clean surfaces. In the deposition, there is no problem when only a channel portion is opened using lithography and the nanoparticles are deposited only in the channel portion. Such a method is described in, for example, a literature "Non-Patent Literature A-2: Sato et al., Sensors and Materials, 21, 373 (2009)" and a literature "Sato et al., Chem. Phys. Lett. 382, 361 (2003)".

Fifth Embodiment

Figure 14A:
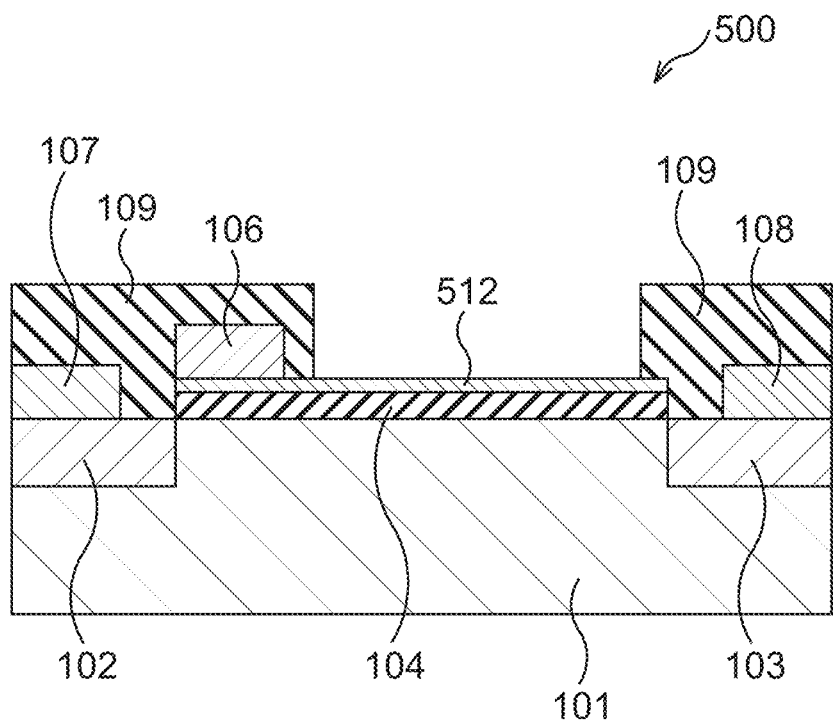
FIG. 14A is a cross-sectional view illustrating a structure of a gas sensor according to a fifth embodiment.

Next, a fifth embodiment will be described. FIG. 14A is a cross-sectional view illustrating a structure of a gas sensor according to the fifth embodiment.

Figure 14B:
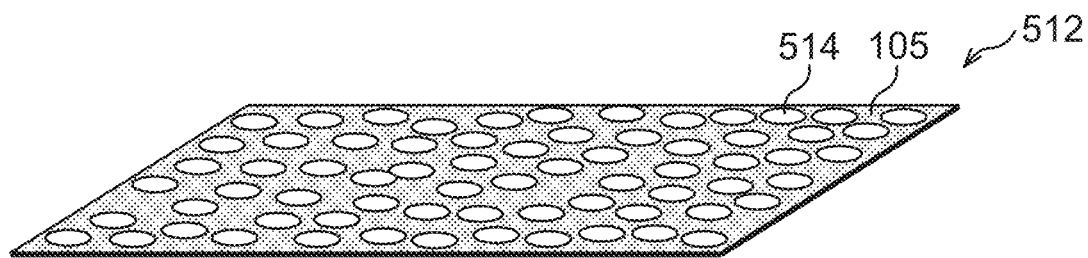
FIG. 14B is a view illustrating a structure of graphene nanomesh.

A gas sensor 500 according to the fifth embodiment includes, as illustrated in FIG. 14A, graphene nanomesh 512 in place of the graphene film 105. The other configuration is the same as that in the first embodiment. The graphene nanomesh 512 is configured such that, as illustrated in FIG. 14B, a plurality of holes 514 are formed, for example, in the graphene film 105. The size and space of the holes 514 are, for example, about 1 nm to 50 nm. The formation of the holes 514 changes the electronic state of the graphene film 105 so that the way for gas molecules to adsorb to the graphene film 105 and the variation in work function accompanying the adsorption are made different. Therefore, the sensitivity differs from that in the first embodiment, and high sensitivity can be exhibited also to gas other than ammonia and nitrogen dioxide.

The edge of the hole 514 may be chemically modified with a specific atom or molecule such as H, F, $NH_2$, $CH_3$, Cl, Br, OH, COOH or the like. The chemical modification can also adjust the reactivity or sensitivity of the gas sensor 500.

Figure 15:
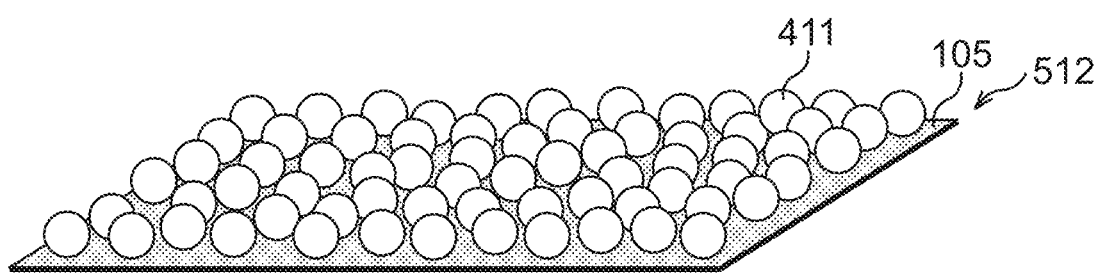
FIG. 15 is a view illustrating a modified example of the fifth embodiment.

The nanoparticles 411 may enter some or all of the holes 514 as illustrated in FIG. 15. Also in this case, the reactivity or sensitivity of the gas sensor 500 can be adjusted. This structure is obtained, for example, by depositing the nanoparticles 411 by laser ablation as in the fourth embodiment and then causing the nanoparticles 411 to absorb carbon of the graphene film 105 by heating. Note that when the nanoparticles 411 absorbed carbon of the graphene film 105 are removed using an acid solution such as a dilute hydrochloric acid or an aqueous iron chloride solution, the graphene nanomesh 512 is obtained.

Examples of the material of the semiconductor layer include a group IV semiconductor, a group III-V semiconductor, a group II-VI semiconductor, an oxide semiconductor, an organic semiconductor, a metal chalcogenide-based semiconductor, a laminar substance semiconductor, a semiconducting carbon nanotube, and a graphene nanoribbon. Examples of the group IV semiconductor include single-crystal Si and polycrystalline Si. Examples of the group III-V semiconductor include an arsenide semiconductor such as GaAs and a nitride semiconductor such as GaN. An example of the group II-VI semiconductor is CdTe. An example of the oxide semiconductor is ZnO. An example of the organic semiconductor is pentacene. An example of the metal chalcogenide-based semiconductor is $MoS_2$. An example of the laminar substance semiconductor is black phosphorus.

Example of the material of the insulating film 104 include a silicon oxide, a silicon nitride, a silicon oxynitride, a germanium oxide, a high dielectric constant insulator, and a laminar insulator. Examples of the high dielectric constant insulator are insulators containing aluminum, titanium, tantalum, or hafnium or an arbitrary combination of them, such as an aluminum oxide and a hafnium oxide. Examples of the laminar insulator include a hexagonal boron nitride (BN) and a hexagonal boron carbonitride (BCN) being a mixed crystal of boron nitride and graphite.

The barrier film is not limited to the insulating film. For example, when a compound semiconductor is used for the semiconductor layer, a group III-V compound semiconductor or a group II-VI compound semiconductor wider in band gap than the compound semiconductor of the semiconductor layer can be used as the barrier film. Examples of the combination of the semiconductor layer and the material of the barrier film include a combination of GaAs and AlGaAs, a combination of InGaAs and InAlAs, and a combination of GaN and AlGaN.

The protective film 109 may be omitted according to the use or environment. The kind of gas being a detection target (gas to be detected) is not limited to ammonia. For example, according to these embodiments, it is also possible to measure the concentration of hydrogen ($H_2$), oxygen ($O_2$), carbon monoxide (CO), water ($H_2O$), ethanol, methanol, and nitrogen dioxide ($NO_2$). The conductivity type of the semiconductor layer in these embodiments may be opposite. More specifically, an n-type layer may be used in place of the p-type layer 101, a p-type layer may be used in place of the n-type layer 102, and a p-type layer may be used in place of the n-type layer 103.

The preferred embodiments of the present invention have been described above in detail, but the present invention is not limited to such examples. It is apparent that a person having common knowledge in the technical field to which the present invention belongs is able to devise various variation or modification examples within the range of technical ideas described in the claims, and it should be understood that such examples belong to the technical scope of the present invention as a matter of course.

The above-described gas sensor includes appropriate graphene film, barrier film, and semiconductor layer and therefore can detect gas such as ammonia with high sensitivity.

The above-described gas sensor includes appropriate graphene film, barrier film, and semiconductor layer and therefore can detect gas such as ammonia with high sensitivity.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A gas sensor comprising:
   a semiconductor layer;
   a graphene film provided above the semiconductor layer having at least a portion in contact with gas;
   a barrier film between the semiconductor layer and the graphene film;
   a pair of impurity conductive regions formed on both sides of the barrier film on the surface of the semiconductor layer by implantating ion into the semiconductor layer; and
   an interlayer insulating film covering the barrier film, wherein:
   the graphene film is provided on the interlayer insulating film; and
   the graphene film is in electrical contact with the barrier film through a conductive layer in the interlayer insulating film.

2. The gas sensor according to claim 1, wherein the graphene film is in contact with the barrier film.

3. The gas sensor according to claim 1, further comprising nanoparticles on the graphene film.

4. The gas sensor according to claim 1, wherein a material of the semiconductor layer is a group IV semiconductor, a group III-V semiconductor, a group II-VI semiconductor, an oxide semiconductor, an organic semiconductor, a metal chalcogenide-based semiconductor, a laminar substance semiconductor, a semiconducting carbon nanotube, or a graphene nanoribbon.

5. The gas sensor according to claim 1, wherein a material of the barrier film is a silicon oxide, a silicon nitride, a silicon oxynitride, a germanium oxide, a high dielectric constant insulator, or a laminar insulator.

6. The gas sensor according to claim 1, wherein:
   a material of the semiconductor layer is a first compound semiconductor;
   a material of the barrier film is a second compound semiconductor; and
   a band gap of the second compound semiconductor is wider than a band gap of the first compound semiconductor.

7. A method of using a gas sensor, comprising:
   detecting a physical amount corresponding to a variation amount in work function of a graphene film using a gas sensor,
   the gas sensor comprising:
   a semiconductor layer;
   a graphene film provided above the semiconductor layer having at least a portion in contact with gas;
   a barrier film between the semiconductor layer and the graphene film;
   a pair of impurity conductive regions formed on both sides of the barrier film on the surface of the semiconductor layer by implantating ion into the semiconductor layer; and
   an interlayer insulating film covering the barrier film, wherein:
   the graphene film is provided on the interlayer insulating film; and
   the graphene film is in electrical contact with the barrier film through a conductive layer in the interlayer insulating film.

* * * * *